United States Patent [19]
Gibson

[11] Patent Number: 5,304,639
[45] Date of Patent: Apr. 19, 1994

[54] METHOD FOR PREPARATION OF GLYCOSIDES

[75] Inventor: Michael W. Gibson, Fairfield, Ohio

[73] Assignee: Henkel Corporation, Plymouth Meeting, Pa.

[21] Appl. No.: 890,520

[22] Filed: May 28, 1992

[51] Int. Cl.$^5$ .................... C07H 15/04; C07G 3/00
[52] U.S. Cl. .................... 536/18.6; 536/127
[58] Field of Search ................ 536/18.6, 127

[56] References Cited

U.S. PATENT DOCUMENTS

| | | | |
|---|---|---|---|
| 2,606,186 | 8/1952 | Dean et al. | 536/18.6 |
| 3,565,885 | 2/1971 | Molotsky et al. | 536/18.6 |
| 3,839,318 | 10/1974 | Mansfield | 536/18.6 |
| 4,223,129 | 9/1980 | Roth et al. | 536/4 |
| 4,393,203 | 7/1983 | Mao et al. | 536/124 |
| 4,721,780 | 1/1988 | McDaniel, Jr. et al. | 536/18.6 |
| 4,939,245 | 7/1990 | Rasche et al. | 536/18.6 |
| 4,950,743 | 8/1990 | McCurry, Jr. et al. | 536/18.6 |
| 4,987,225 | 1/1991 | Pickens et al. | 536/18.6 |
| 5,003,057 | 3/1991 | McCurry et al. | 536/18.6 |
| 5,079,350 | 1/1992 | Fujita et al. | 536/18.6 |
| 5,138,046 | 8/1992 | Wuest et al. | 536/18.6 |

FOREIGN PATENT DOCUMENTS 0077167 4/1983 European Pat. Off. .

OTHER PUBLICATIONS

"Kirk Othmer Encyclopedia of Chemical Technology", vol. 9, pp. 472-493 (1980), third edition.

*Primary Examiner*—John Kight, III
*Assistant Examiner*—Jeffrey Culpeper Mullis
*Attorney, Agent, or Firm*—Wayne C. Jaeschke; John E. Drach; Daniel S. Ortiz

[57] ABSTRACT

The invention is a process for reducing the fatty alcohol content of a mixture of fatty alcohol and fatty glycoside product by passing the mixture through a forced circulation evaporation zone to form a mixture of fatty alcohol and fatty glycoside product with a reduced fatty alcohol content and passing the mixture with the reduced fatty alcohol content to a wiped film evaporator to remove additional fatty alcohol.

10 Claims, 1 Drawing Sheet

METHOD FOR PREPARATION OF GLYCOSIDES

BACKGROUND OF THE INVENTION

Glycoside surfactants have been known for at least sixty years. They are nonionic surfactants with low toxicity and gentleness to the skin. They can be made from renewable resources and are rapidly degraded in the environment.

In spite of the excellent properties of the glycoside surfactants, they have not achieved great commercial acceptance because of the difficulties encountered in their production. Rohm & Haas Corporation has been providing alkyl glycosides in which the alkyl group is formed from a mixture of fatty alcohols having 8 and 10 carbon atoms. The compositions are sold under the trade names BG-10 and CG-110. The BG-10 composition is a dark, almost black material and is used only in commercial formulations. The CG-110 material is a light colored product useful for consumer applications.

Early processes for the preparation of glycoside surfactants were two-step processes. The first step comprised the reaction of a lower alcohol having 1 to 6 carbon atoms with a saccharide source in the presence of an acid catalyst to form a glycoside. The glycosides prepared from the lower alcohols did not have useful surfactant properties. Since water is soluble in the alcohols, the reaction mixture could contain a substantial quantity of water (see U.S. Pat. No. 4,721,780). The higher glycoside surfactants in which the organic group attached to the glycoside moiety contains more than about 7 carbon atoms are then prepared by transacetalization of the lower glycoside with alcohols containing at least 7 carbon atoms under substantially anhydrous conditions.

More recently, aliphatic glycosides having aliphatic groups with from 7 to 22 carbon atoms have been prepared by a "direct process". In the "direct process" a long chain fatty alcohol is reacted with a source of saccharide in the presence of an acid catalyst under conditions in which the water formed in the reaction is removed as quickly as it is formed to maintain the water content of the reaction mixture at as low a level as is reasonably possible. The water formed in the reaction is only sparingly soluble in the fatty alcohol and any undissolved water results in the rapid formation of unwanted byproducts. The parameters of the "direct process" with a less than ideal catalyst and neutralization procedure are disclosed in U.S. Pat. No. 3,839,318, which is incorporated herein by reference. Other patents such as U.S. Pat. No. 4,939,245, U.S. Pat. No. 4,950,743 and U.S. Pat. No. 5,003,057 also disclose the "direct process" and are incorporated herein by reference.

The glycoside surfactants are formed by the reaction of the alcohol having more than about 7 carbon atoms and preferably more than about 8 carbon atoms with a saccharide source under anhydrous conditions in the presence of an acid catalyst. The reaction is generally carried out in the presence of a stoichiometric excess of the alcohol and at least a sufficient amount of alcohol to maintain the reaction mixture in a fluid state. Generally, the reaction mixture contains from about 1.5 to about 10 moles of alcohol per mole of saccharide moiety.

The reaction is carried out at a temperature in the range of from about 90° C. to about 145° C. under a reduced pressure. The high temperature and reduced pressure provide for rapid removal of the water formed in the reaction from the reaction mixture. The temperature and reduced pressure at which the reaction is carried out is dependent upon the alcohol used and the amount of discoloration which can be tolerated in the finished product. The lower molecular weight alcohols generally react at lower temperatures and at higher pressures, since at lower pressures the lower molecular weight alcohols tend to vaporize and change the composition of the reacting mixture.

After the source of saccharide has been substantially all reacted with the alcohols or polymerized to form a polymer, the acid catalyst is neutralized.

After the catalyst has been neutralized, it is generally accepted procedure that the unreacted or excess alcohol is then separated from the reaction mixture. Generally, it is desirable to have as low a content of the higher alcohol in the product as possible. The presence of higher alcohols are known to reduce the surfactant activity of the composition and to impact the odor of the product. Generally, the amount of alcohol remaining in the product is generally less than about 5% by weight of the product and preferably less than about 2% by weight and most preferably less than about 1.0% by weight of the product.

The alcohol is generally removed from the reaction mixture by heating the reaction mixture at a reduced pressure. Preferably, the alcohol is separated from the glycoside product in a thin film evaporator such as disclosed in U.S. Pat. No. 4,223,129 or EP 077 167. U.S. Pat. No. 3,565,885 and U.S. Pat. No. 4,393,203 disclose that the most preferred method for removing the unreacted alcohol from the reaction mixture is in a wiped film evaporator. Especially with longer chain alcohols, a wiped film evaporator is particularly useful in that the glycoside product is exposed to the high temperature for only a short period of time and the degradation caused by the vaporization process is substantially reduced.

U.S. Pat. No. 5,079,350 discloses that the most preferred method for removing unreacted alcohol from a glycoside surfactant product is to contact the alkyl glycoside and alcohol mixture with a stream of inert gas under reduced pressure in a wiped film evaporator maintained at a temperature in the range of about 140° C. to about 200° C. The process is disclosed as substantially removing all of the unreacted alcohol and odor from the glycoside product.

Wiped film evaporators have been recognized as being useful for removing high boiling point materials from heat sensitive products. However, wiped film evaporators are an expensive apparatus and have a limited surface area for a unit volume of the evaporator. It would be advantageous to be able to reduce the evaporation load which is required of the wiped film evaporator. The prior art teaches that the glycoside products are sensitive to heat and the color of the product deteriorates when the reaction mixture is exposed to a high temperature for a relatively long period of time. One skilled in the art faced with the problem of removing unreacted fatty alcohol from a glycoside product would select a process in which the glycoside product is exposed to an elevated temperature for as short a period of time as possible.

BRIEF DESCRIPTION OF THE INVENTION

Applicants have unexpectedly discovered that the unreacted fatty alcohol can be readily removed from a reaction product containing a fatty alcohol and a fatty glycoside by first passing a mixture of fatty alcohol and fatty glycoside through an intermediate evaporation zone such as a falling film or forced circulation evaporation zone operated at a temperature in the range of about 140° C. to about 220° C. and a pressure in the range of from about 1.0 millimeters Hg to about 100 millimeters Hg to remove a portion of the alcohol from the fatty glycoside then passing the fatty glycoside with the reduced alcohol content from the forced circulation or falling film evaporation zone directly to a wiped film evaporation zone. Preferably the intermediate evaporation zone is a forced circulation evaporation zone.

The fatty glycoside entering the wiped film evaporation zone generally has a substantial portion of the fatty alcohol present in the original mixture removed and contains from about 10% by weight to about 60% by weight of fatty alcohol. The fatty alcohol content of the fatty glycoside is reduced in the wiped film evaporation zone to a range of less than about 5% by weight of the mixture of fatty alcohol and fatty glycoside and preferably less than about 2% by weight of the mixture and most preferably less than about 1.0% by weight of the mixture of alcohol and fatty glycoside.

The quantity of unreacted alcohol in the mixture of fatty glycoside and fatty alcohol which is passed on to the wiped film evaporation zone is in the range of about 10% to 60% by weight of the mixture, preferably less than 50% by weight of the mixture and most preferably in the range of from about 25% to about 40% by weight of the mixture. Since the reaction mixture containing the fatty glycoside generally contains from about 50% to about 80% by weight of unreacted fatty alcohol, the reduction in the vaporization load on the wiped film evaporator is substantial.

BRIEF DESCRIPTION OF THE FIGURE

The FIGURE is a diagrammatic representation of a fatty alcohol removal process of the invention.

DETAILED DESCRIPTION OF THE INVENTION

Figure 1:
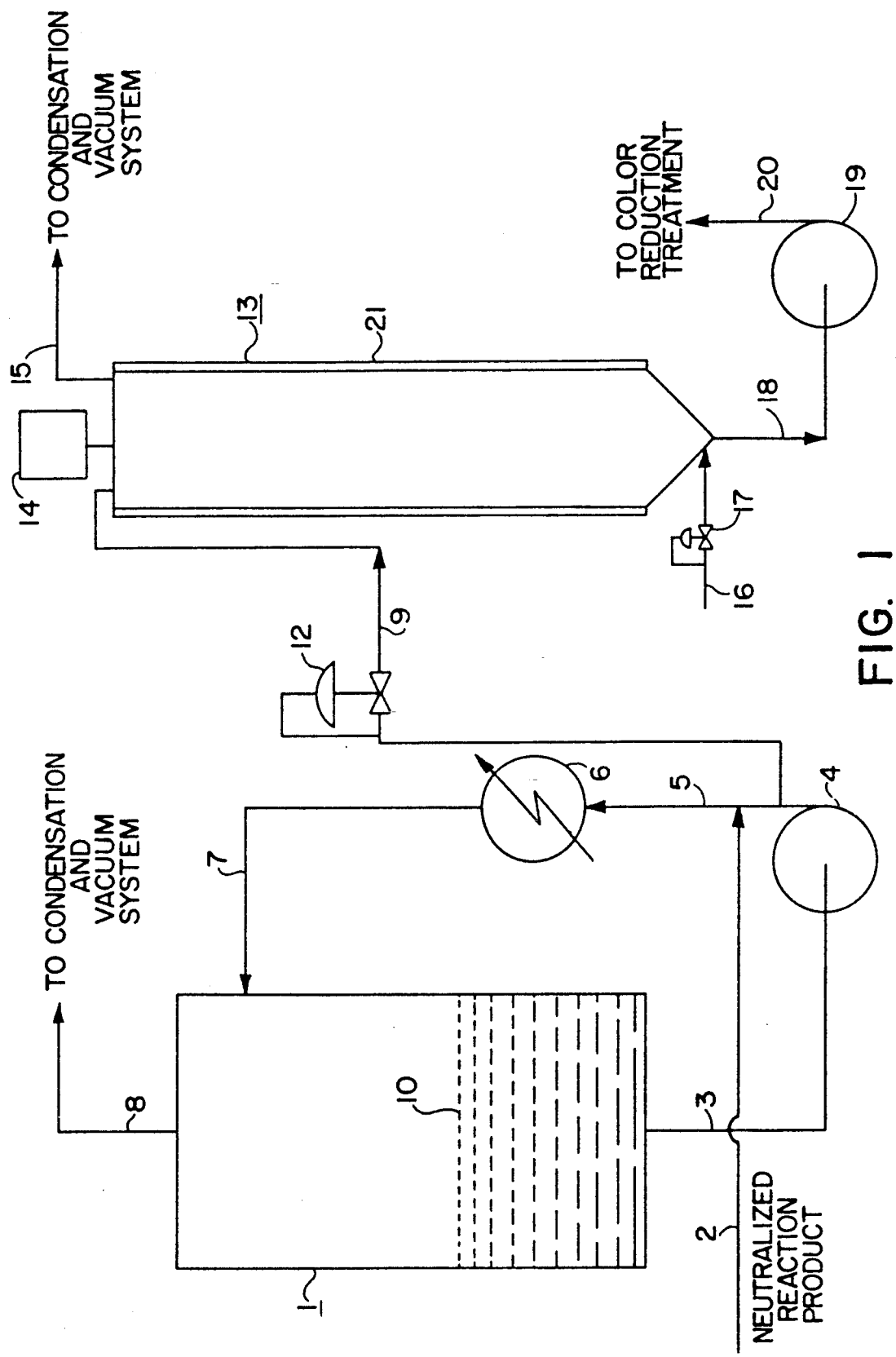

The term "fatty alcohol" as used herein refers to alcohols having from 7 to about 22 carbon atoms. The alcohols can be saturated or unsaturated, straight chain or branched. The alcohols can contain saturated cyclic or unsaturated cyclic or aromatic moieties. Preferably, the fatty alcohol is an aliphatic alcohol having from 8 to about 18 carbon atoms and most preferably from about 8 to about 16 carbon atoms. Alcohols having aromatic or other cyclic moieties in their structure can also be reacted to form fatty glycoside products, but the fatty glycoside products are generally not as biodegradable as the fatty glycoside products formed from aliphatic alcohols.

As used herein, a saccharide source refers to a reducing sugar or an oligomer or polymer comprising moieties of a reducing sugar which under the acid conditions of the process forms a reducing saccharide required to react with the alcohol. Materials such as dextrose, high dextrose corn syrup and the like have been found useful to prepare the glycosides by the improved process of the invention.

The term "fatty glycoside" is used herein to denote a composition of the formula

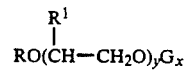

wherein R is the residue of an alcohol having from about 7 to about 22 carbon atoms, preferably from about 8 to 18 carbon atoms and most preferably from about 8 to about 16 carbon atoms; $R^1$ is H, $CH_3$ or $CH_2CH_3$, G is the residue of a reducing saccharide; y is a number of from 0 to about 5; and x is a number of from 1 to about 5.

G is the residue of a reducing saccharide. The reducing saccharide can be a monosaccharide such as glucose, fructose, galactose, mannose, xylose, lactose and the like or the residue or fragments of a polysaccharide or oligosaccharide such as sucrose, maltose, isomaltose, maltotriose, cellobiose, mellobiose and the like.

The fatty glycoside can be formed by the two step process or the direct process since both processes produce reaction mixtures which contain unreacted fatty alcohol which must be removed from the fatty glycoside product. However, the two step process reaction mixture generally contains some unreacted lower alcohol glycoside (1 to 6 carbon atoms) and some lower alcohol (1–6 carbon atoms) the lower alcohol must also be removed from the fatty glycoside product.

After the alcohol has reacted with the source of saccharide to form the fatty glycoside, the reaction mixture is then neutralized (pH above about 7) and preferably the pH is increased to the range of about 9 to 12 and preferably between about 9.2 and about 10.5 The acid can be neutralized by contact with an alkali metal hydroxide or an alkali earth metal oxide or hydroxide or aluminum hydroxide or aluminum oxide. Preferably, the reaction mixture is neutralized with a mixture of alkali earth metal oxide and an alkali metal hydroxide. The presence of the alkali metal hydroxide is necessary to ensure that the pH of the mixture is maintained in a suitable range.

As part of the neutralization, a color improving and color stabilizing material such as an alkali metal borohydride or the like can be added to the reaction mixture. It has been believed advantageous in the past to introduce into the reaction mixture a mixture of an alkali metal hydroxide and a material such as sodium borohydride. The alkali metal hydroxide neutralizes the acid catalyst and the sodium borohydride improves the color properties of the mixture. However, it is preferred that the mixture be neutralized to a pH in the range of from about 9 to 12 with alkali metal hydroxide and alkali earth metal oxide or hydroxide addition and passed to the zone wherein the amount of alcohol in the glycoside product is reduced.

Generally, the neutralized reaction product contains from about 15% to about 50% by weight of the fatty glycoside product and from about 50% to about 85% by weight of unreacted fatty alcohol. The neutralized and optionally color improved reaction product is then passed to a zone wherein the unreacted fatty alcohol is separated from the fatty glycoside product. As is known in the art, the fatty alcohol can be separated from the fatty glycoside product in a thin film evaporation zone.

Applicants have discovered that a more efficient method for separating the fatty alcohol from the fatty glycoside product can be provided which utilizes a forced circulation evaporation zone or falling film evaporation zone to remove a substantial portion of the unreacted fatty alcohol then passing the fatty glycoside product with a reduced content of unreacted fatty alcohol to a wiped film evaporation zone to reduce the content of free fatty alcohol in the fatty glycoside product to less than about 5% by weight, preferably less than about 2% by weight, and most preferably less than about 1.0% by weight of the mixture of fatty alcohol and fatty glycoside product.

Preferably the neutralized and optionally color improved reaction product containing the unreacted fatty alcohol and the fatty glycoside product is passed to a forced circulation evaporation zone. In the forced circulation evaporation zone, a reservoir of the reaction mixture having a portion of the fatty alcohol removed is maintained under a reduced pressure and at an elevated temperature. The pressure is generally in the range of from about 1.0 millimeters Hg to about 100 millimeters Hg and a temperature in the range of from about 140° C. to about 220° C. The product is pumped through a heat exchange means at a rate to maintain a velocity of from about 2 to about 25 feet per second in the heat exchanger and then introduced into the forced circulation evaporating zone vessel above a reservoir of the fatty glycoside with the reduced fatty alcohol content. The stream of material which has passed through the heat exchange means can be sprayed over the top of the reservoir or introduced tangentially at points along the sides of the vessel containing the reservoir of fatty glycoside product with the reduced content of fatty alcohol.

The temperature of the heating material for the heat exchange means is generally maintained as close as possible to the required temperature of the circulating liquid stream. Preferably, the differential temperature between the heating material and the circulating liquid is in the range of less than about 40° C., preferably less than about 30° C. and most preferably less than about 20° C. The liquid passing through the heat exchange means is maintained at a relatively high velocity to improve the heat transfer rate and reduce the difference in the temperature between the heating material and the circulating liquid to as low a value as practical. A restriction means such as a valve or an orifice is generally provided in the circulating system downstream of the heat exchange means to prevent boiling of the circulating liquid in the heat exchange means.

The neutralized reaction product which is introduced into the forced circulation evaporating zone can be introduced into the body of the liquid in the reservoir in the forced circulating evaporating vessel introduced into the suction or the discharge of the circulating pump so that the material is rapidly heated along with the circulating stream of the fatty glycoside product with the reduced fatty alcohol content.

The forced circulation evaporating zone can have mist elimination means to remove any materials which may tend to leave the forced circulation evaporation zone with the fatty alcohol vapors which are being separated from the fatty glycoside product. In addition, a stream of inert gas can be introduced into the reservoir of fatty glycoside product or into the vapor space above the reservoir of the fatty glycoside product to assist in reducing the content of fatty alcohol in the mixture. The forced circulating evaporating zone can be operated on a batch or a continuous basis. That is, the neutralized reaction product is introduced into the forced circulation evaporating zone and the reservoir of material circulated through the heat exchange means and returned to the reservoir of material in the forced circulating evaporating vessel until a composition with the desired content of fatty alcohol has been provided. At this point, a stream of the reaction product with reduced alcohol content is continuously introduced into the wiped film evaporation zone.

Preferably, the forced circulation evaporating zone is operated continuously wherein a stream of the neutralized reaction product is introduced continuously into the forced circulation evaporation zone and a stream of the forced evaporation zone product is introduced continuously into the wiped film evaporation zone.

Wiped film evaporators are well known in the art of separating high boiling point materials from heat sensitive products. In the wiped film evaporating zone, the feed comprising fatty alcohol and fatty glycoside product is introduced into the zone along the peripheral surface of the evaporator and a series of wiper blades rotating in the wiped film evaporation zone continuously wipe and spread the mixture over the heated surfaces of the wiped film evaporating zone. The heated surfaces of the wiped film evaporation zone can be heated by well known means such as hot oil, steam or even electrically as the case may require.

The wiped film evaporation zone is generally operated at a temperature and pressure to provide a product with the required fatty alcohol content. The temperature and pressure required in the wiped film evaporation zone is dependent upon the fatty alcohol which must be removed and the level of fatty alcohol permitted in the fatty glycoside product. Generally, the wiped film evaporator is operated at a pressure in the range of from about 0.1 millimeters to about 70 millimeters Hg, preferably from about 1.0 millimeters to about 40 millimeters Hg and a product temperature in the range of from about 150° C. to about 230° C.

The removal of the fatty alcohol from the fatty glycoside product can be carried out at a reduced temperature if an inert gas is introduced into the lower portion of the wiped film evaporator to reduce the partial pressure of the fatty alcohol above the fatty glycoside product. The inert gas can be introduced into the wiped film evaporator at the lower portion and preferably below the level at which the wiper means spreads the layer of fatty glycoside product on the heated surface of the wiped film evaporator.

The process will be described in relation to the FIGURE. The FIGURE shows forced circulation evaporation vessel 1 containing reservoir 10 of fatty glycoside product having a reduced level of fatty alcohol. The neutralized reaction product enters the forced circulation evaporation zone through line 2. The neutralized reaction product at a pH above about 7 passes to line 5 which is at the discharge of forced circulating pump 4. The mixture of the neutralized reaction product and the circulating stream from forced circulation evaporation vessel 1 passes through heat exchanger 6, line 7 and is returned to the vapor space of the forced circulation evaporation vessel 1. The ratio of circulating liquid from forced circulation evaporation vessel 1 and the feed of neutralized reaction product is in the range of from about 3:1 to about 40:1 and preferably from about 5:1 to about 25:1.

The heated stream from line 7 enters the forced circulation evaporation vessel 1 in the vapor space above the reservoir of liquid 10. The heated liquid can be sprayed into the vapor space, can enter as a solid stream or can be introduced tangentially along the walls to form a thin layer of the mixture. A pressure in the range of from about 1 millimeter Hg to about 100 millimeters Hg pressure is maintained in forced circulation evaporation vessel 1. Preferably, the pressure is maintained in the range of from about 5 millimeters Hg to about 70 millimeters Hg and most preferably from about 10 millimeters to about 50 millimeters Hg. The temperature of liquid 10 in forced circulation evaporation vessel 1 is maintained in the range of from about 140° C. to about 220° C. and preferably in the range of from about 150° C. to about 190° C.

The temperature of liquid 10 in the vessel 1 is maintained by circulating a stream of the liquid in vessel 1 through line 3, pump 4, line 5, heat exchanger 6 and line 7 returning to the vapor space in forced circulation vessel 1. The heat exchange means 6 is preferably a shell-in-tube heat exchange means with the forced circulation in the tube side. The velocity of the circulating liquid is maintained as high as practical and preferably in the range of from about 2 feet to about 25 feet per second, preferably from about 5 to about 20 feet per second and most preferably in the range of about 7 to about 15 feet per second. The rapid flow improves the heat transfer and reduces the fouling of the heat exchange surfaces.

A flow restriction means such as a control valve, an orifice plate or other means (not shown) is positioned in line 7 downstream of heat exchange means 6 to prevent or minimize any boiling which may occur in heat exchange means 6 to reduce fouling of the heat transfer surfaces. Heat exchange means 6 can be heated by hot oil, high pressure steam or other means known for providing a source of heat to a tube-in-shell heat exchanger. The heating media is on the shell side of the heat exchange means.

A vacuum is maintained in forced circulation evaporation vessel 1 by means of a condensation and vacuum system (not shown) which removes the vapor from the vapor space in vessel 1. As would be well understood in the art, a mist eliminator would generally be incorporated in vessel 1 to maintain the amount of liquid droplets entrained in the vapor stream at a low level. Heat exchangers to condense vaporized fatty alcohol, ejectors and vacuum pumps (not shown) generally comprise a vacuum producing system.

When the system is initially started, a reservoir of the neutralized reaction product is collected in forced circulation evaporation vessel 1. When the level in the vessel has reached the point that circulation to the pump suction can be assured, pump 4 is placed in operation, the vacuum producing means in communication with vessel 1 through line 8 is placed in operation, and heating material is introduced into the shell of heat exchange means 6. The liquid 10 in vessel 1 is circulated through heat exchange means 6 to vaporize the fatty alcohol until a desired level of glycoside product in the fatty alcohol has been attained. Generally, a sufficient amount of fatty alcohol is evaporated to provide a fatty glycoside product containing from about 20% to about 50% and preferably from about 25% to about 40% fatty alcohol in the glycoside product in reservoir 10 in forced circulation evaporation vessel 1.

When the desired concentration of fatty glycoside product and fatty alcohol have been attained in liquid 10 in vessel 1, control valve 12 is opened and a continuous feed of liquid 10 from the reservoir is introduced through line 9 into wiped film evaporator 13. The rate of flow of liquid 10 from the reservoir to wiped film evaporator 13 can be controlled by the level of liquid 10 in vessel 1, by flow control or other means. Preferably, the flow of liquid 10 to wiped film evaporator 13 is done by flow control of the liquid in line 9 since a constant flow provides for more even operation of the wiped film evaporator and a more uniform product.

The rate of flow of the neutralized reaction product into the forced circulation evaporation vessel 1 and the flow rate of the liquid to wiped film evaporator 13 through line 9 is controlled so that the flow is continuous and the amount of liquid 10 in the reservoir in forced circulation evaporation vessel 1 is maintained relatively constant. The flow rate of the neutralized reaction product into the forced circulation evaporation zone can be controlled and the pressure and amount of heating done in heat exchange means 6 can be controlled to provide a balanced flow of neutralized reaction product into the system and fatty glycoside product with a reduced fatty alcohol content out of the system.

The amount of fatty alcohol which is removed from the mixture of fatty glycoside product and fatty alcohol in the forced circulation evaporation zone is dependent upon the molecular weight of the fatty alcohol, the temperature to which circulating liquid 10 in forced circulation evaporation vessel 1 is heated, the pressure maintained in vessel 1 and the amount of fatty alcohol in the neutralized reaction product entering forced circulation evaporation vessel 1. The temperature at which liquid 10 in the reservoir of forced circulation evaporation vessel 1 is maintained and the pressure provided in the vapor space of vessel 1 determines the amount of fatty alcohol which is removed from the mixture of the fatty glycoside product and fatty alcohol.

Generally, the feed entering the wiped film evaporation zone contains from about 25% to about 50% by weight of fatty alcohol. This generally entails removing from about 35% to about 65% of the fatty alcohol from the neutralized mixture in the forced circulation evaporation zone. The removal of the substantial portion of the fatty alcohol at relatively mild temperature conditions in the forced circulation evaporation zone substantially reduces the thermal stress on the glycoside product and the amount of feed and the vaporization load which is placed on the wiped film evaporation zone.

The discharge from the forced circulation evaporation zone enters the wiped film evaporator through line 9. The liquid flows along the heat exchange surfaces of the evaporator and is wiped by rotating blades on the film wiping means. The shell of the vessel can be heated by high pressure steam, hot oil or electricity. However, the most suitable control is obtained by circulating hot oil or utilizing high pressure steam as the heating medium in the jacket of vessel 13. The rotating wiper blades are rotated by wiper rotating means 14 which is generally an electric motor adjusted by means of gearing or speed control to rotate the wiper blades at the required tip speed. Generally, the wiper blades are rotated to provide a turbulent film layer on the heat exchange surfaces of the wiped film evaporator.

Preferably a small amount of an inert gas is introduced into wiped film evaporator 13 through line 16 and control valve 17. The amount of steam (if using ejectors) and/or inert gas entering the system can be on flow control (as shown) or can be utilized to control the pressure in the system. The addition of the inert gas at the product outlet portion of the wiped film evaporator reduces the partial pressure of the fatty alcohol in the vapor phase and therefore can aid in reducing the amount of fatty alcohol which remains in the fatty glycoside product or in the alternative reduce the temperature at which the fatty glycoside product must be heated to reduce the fatty alcohol content to a level below about 1% and preferably below about 0.5% by weight. The fatty glycoside product leaves the wiped film evaporation zone through line 18, pump 19 and line 20 to a color reduction treatment and product concentration adjustment zone.

As is well known in the art, the fatty glycosides as produced generally have a color which is much darker than required for use in consumer products. In addition, the fatty glycoside product contains very little fatty alcohol and is in the range of about 95% to about 98% fatty glycoside by weight. The high concentration of the fatty glycoside makes the product a high melting point solid which is generally not suitable for further processing. The fatty glycoside product generally contains from about 2 to about 5% by weight of materials such as neutralized catalyst, fatty alcohol, polydextrose and the like.

In one embodiment of the invention, water is introduced into the glycoside product leaving the wiped film evaporation zone through line 20 to form an aqueous mixture containing from about 30% to about 85% by weight of the fatty glycoside. The product which has been diluted has a viscosity which is relatively easily handled in the processing plant. The glycoside product can be treated with hypochlorite, peroxide, or other means to reduce the color of the fatty glycoside product. The product can be hydrogenated over a catalyst or treated with an alkali metal borohydride to further reduce the color and to stabilize the color against deterioration over long periods of storage.

After the color correction and stabilization treatment, the pH and concentration of the fatty glycoside product is adjusted to the required range, the color determined and the material placed in storage for sale. The arrangements of the various pumping means, heat exchange means, flow control means and the like can be varied to suit a particular installation without falling outside of the process of the invention.

We claim:

1. A method for reducing the content of fatting alcohol in a mixture of fatty alcohol and fatty glycoside product which comprises:
   a) continuously introducing a first mixture comprising fatty alcohol and fatty glycoside product into a forced circulation evaporation zone operated at a temperature of from abut 140° C. to about 220° C. and a pressure of from about 1.0 millimeter Hg absolute to about 100 millimeters Hg absolute to remove fatty alcohol from the first mixture and produce a mixture comprising fatty alcohol and fatty glycoside product with reduced fatty alcohol content; and
   b) passing the mixture comprising fatty alcohol and fatty glycoside product with reduced fatty alcohol content continuously from the forced circulation evaporization zone into a wiped film evaporization zone operated at a temperature of from 140° C. to about 240° C. and a pressure of from about 0.1 millimeter Hg absolute to about 90 millimeters Hg absolute to remove fatty alcohol and produce a fatty glycoside product containing less than about 5% by weight of fatty alcohol.

2. A method of claim 1 wherein the fatty glycoside product is an aliphatic glycoside having an aliphatic moiety containing from about 8 to about 20 carbon atoms.

3. A process of claim 1 wherein the fatty glycoside product contains less than about 1% by weight of fatty alcohol.

4. A process of claim 1 wherein the forced circulation evaporization zone is maintained at a pressure of from abut 5 millimeters Hg absolute to about 20 mm Hg absolute and a temperature of from about 150° C. to about 175° C.

5. A process of claim 1 wherein the fatty alcohol content of the mixture of fatty alcohol and fatty glycoside product entering the forced circulation evaporization zone is from 50% by weight to about 80% by weight.

6. A process of claim 1 wherein the mixture of fatty alcohol and fatty glycoside product with reduced fatty alcohol content introduced into the wiped film evaporation zone contains from about 60% by weight to about 10% by weight of fatty alcohol.

7. A process of claim 1 wherein the flow of the mixture of fatty alcohol and fatty glycoside product with the reduced fatty alcohol content into the wiped film evaporation zone is controlled by a flow control means.

8. A process of claim 1 wherein the fatty glycoside product is an aliphatic glycoside having an aliphatic moiety containing from about 8 to about 16 carbon atoms.

9. A process of claim 1 wherein the fatty glycoside product comprises an aliphatic glucoside.

10. A process of claim 1 wherein the forced circulation evaporization zone is maintained at a pressure of from about 5 millimeters Hg to about 20 mm Hg.

* * * * *